United States Patent [19]

Hayman et al.

[11] Patent Number: 4,837,336
[45] Date of Patent: Jun. 6, 1989

[54] PROCESS FOR PREPARING HETEROCYCLIC COMPOUNDS

[75] Inventors: David F. Hayman, Bucks; Alastair C. Brodie, Uxbridge; Panayiotis A. Procopiou, Harrow, all of England

[73] Assignee: Glaxo Group Limited, London, England

[21] Appl. No.: 922,255

[22] Filed: Oct. 23, 1986

[30] Foreign Application Priority Data

Oct. 23, 1985 [GB] United Kingdom ................. 8526209

[51] Int. Cl.[4] .................. C07D 498/04; C07D 319/20
[52] U.S. Cl. ..................................... 548/430; 549/362
[58] Field of Search ................. 549/362; 548/430, 431

[56] References Cited

U.S. PATENT DOCUMENTS

| | | | |
|---|---|---|---|
| 3,484,448 | 12/1969 | Kramer et al. | 549/362 X |
| 3,829,441 | 8/1974 | Gardner | 549/366 |
| 3,992,432 | 11/1976 | Napier et al. | 558/344 |
| 4,104,396 | 8/1978 | Huebner | 424/267 |
| 4,212,808 | 7/1980 | Gachwend et al. | 260/340.3 |
| 4,496,579 | 1/1985 | Crame et al. | 548/430 |

FOREIGN PATENT DOCUMENTS

| | | |
|---|---|---|
| 3316 | 1/1978 | European Pat. Off. . |
| 78580 | 10/1960 | France . |
| 565573 | 1/1943 | United Kingdom . |
| 1001479 | 8/1965 | United Kingdom . |
| 1089704 | 11/1967 | United Kingdom . |
| 1330652 | 9/1975 | United Kingdom . |
| 1544647 | 4/1979 | United Kingdom . |

OTHER PUBLICATIONS

Yamamoto, "Cyclisation of Phenol- and Enol-Acetylenes, etc.", J. Chem. Soc., Perkin Trans I, 1979 (12), 3161-3165.
Derwent Abstract 84-095516.
Fieser et al., Reagents for Organic Sythesis, 2, pp. 301, 328-329 (19).

Primary Examiner—John W. Rollins
Assistant Examiner—W. Catchpole
Attorney, Agent, or Firm—Morgan & Finnegan

[57] ABSTRACT

A compound of formula (I)

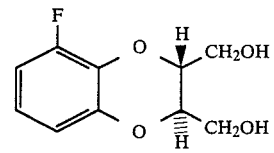

is prepared by cyclizing a compound of formula (IIa) or (IIb) or a mixture thereof

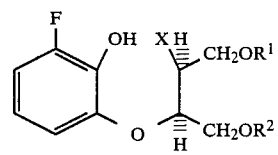

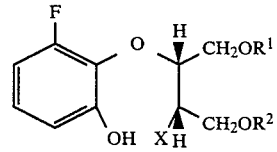

wherein X is hydroxyl or halogen and
$R^1$ and $R^2$ independently, represent hydroxy protecting groups) followed by removal of the protecting groups $R^1$ and $R^2$.

The compound (I) is of use as an intermediate in the stereoselective preparation of ($\pm$) trans-5-fluoro-2,3,3a,9a-tetrahydro-1H-[1,4]benzodioxino[2,3-c] pyrrole, which is a selective $\alpha_2$-adrenoreceptor antagonist and is thus of potential value, in particular, for the treatment or prevention of depression.

2 Claims, No Drawings

PROCESS FOR PREPARING HETEROCYCLIC COMPOUNDS

This invention relates to improvements in the preparation of trans-5-fluoro-2,3,3a,9a-tetrahydro-1H-[1,4]benzodioxino [2,3-c]pyrrole and N-alkyl substituted derivatives thereof. In particular it relates to intermediates which are of value in the stereoselective preparation of ($\pm$) trans- 5l -fluoro- 2,3,3a,9a-tetrahydro-1H-[1,4]benzodioxino[2,3-c]pyrrole.

($\pm$) trans- 5l -fluoro- 2,3,3a,9a-tetrahydro- 1H-[1,4]-benzodioxino[2,3-c]pyrrole is described in our European Patent Application No. 85302854.6. 1 It is a selective $\alpha_2$-adrenoreceptor antagonist and is thus of potential value in the treatment or prevention of migraine, thrombosis, diabetes, obesity, hypotension, constipation, paralytic ileus and senile dementia, and in particular for the treatment of depression, either alone or when co-administered with an established antidepressant.

A key intermediate in the preparation of ($\pm$) trans-5-fluoro-2,3,3a,9a-tetrahydro-1H-[1,4]-benzodioxino-[2,3-c]pyrrole is the diol of formula (I)

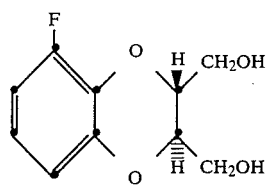

We have now found a new and advantageous process for the preparation of this intermediate.

Thus, according to one feature of the present invention the compound of formula (I) may be prepared by cyclising a compound of formula (IIa) or (IIb) or a mixture thereof

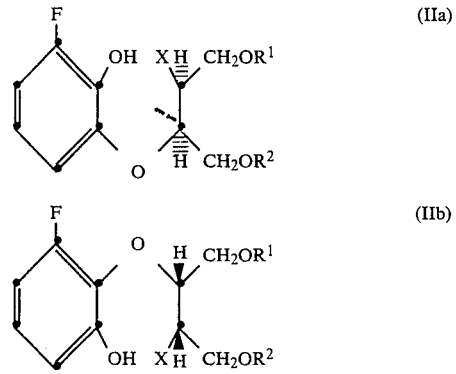

(wherein X represents a hydroxyl group or a halogen atom e.g. a chlorine atom and $R^1$ and $R^2$, which may be the same or different, represent hydroxy protecting groups) followed by removal of the protecting groups $R^1$ and $R^2$.

When X represents a hydroxyl group the cyclisation may be effected using a disubstituted formamide e.g. dimethylformamide in the presence of a reagent such as oxalyl chloride, thionyl chloride, phosgene or phosphorus oxychloride (POCl$_3$) and a base e.g. a trialkylamne such as triethylamine. The reaction is preferably carried out in a solvent such as halogenated hydrocarbon e.g. methylene chloride or an aromatic hydrocarbon e.g. toluene at a temperature in the range of from room temperature to reflux. Alternatively, the reaction may be effected using a triarylphosphine such as triphenylphosphine, a trialkylphosphine or a trialkylphosphite in the presence of diethyl azodicarboxylate (DEADCAT) or using a triarylphosphine or trialkylphosphine in the presence of carbon tetrachloride. When DEADCAT is used the reaction is carried out in a solvent such as tetrahydrofuran or acetonitrile preferably with heating e.g. at reflux. When carbon tetrachloride is used the reaction is carried out in a solvent such as acetonitrile and in the presence of a base e.g. triethylamine with heating e.g. at reflux.

When X represents a halogen atom e.g. a chlorine atom the cyclisation may be effected in the presence of a base such as an alkali metal carbonate e.g. sodium carbonate, cesium carbonate or potassium carbonate preferably with heating eg at reflux in a solvent such as a ketone (e.g. acetone), dioxane, acetonitrile and/or water. Advantageous conditions for carrying out the reaction include using potassium carbonate as the base and water as the solvent. A two-phase solvent system may also be used, involving for example water, and a haloalkane e.g. dichloromethane or, more preferably, an aromatic hydrocarbon e.g. toluene. The cyclisation may also conveniently be carried out in the presence of a suitable phase transfer catalyst such as a tetraalkyammonium salt e.g. tetrabutylammonium chloride, tetrabutylammonium iodide or tricaprylylmethylammonium chloride.

It will be appreciated that compounds of general formulae (I) to (VIII) exist as two enantiomers. The formulae (I) to (VIII) herein are to be understood to depict either enantiomer of each compound as well as mixtures of enantiomers, including the racemates although the precise structure as set out only relate to one enantiomer.

Examples of suitable hydroxy protecting groups represented by $R^1$ and $R^2$, are alkyl, alkoxycarbonyl, arylmethyl, acyl, tri(hydrocarbyl)silyl or tetrahydropyranyl groups.

Thus, for example $R^1$ and/or $R^2$ may each represent a group selected from straight or branched C$_1$ 14 6 alkyl [optionally substituted by one or more halogen atoms, or a C$_{1-6}$ alkoxy (which may itself be substituted by one or more halogen atoms or a C$_{1-6}$ alkoxy or rimethylsilyl group) or benzyloxy group], C$_{1-6}$ alkoxycarbonyl (optionally substituted by one or more halogen atoms), C$_{7-20}$ arylmethyl, C$_{1-6}$ alkanoyl (optionally substituted by one or more halogen atoms or C$_{1-3}$ alkyl groups or a C$_{1-3}$ alkoxy, phenoxy or p-chlorophenoxy group), aralkanoyl, aroyl (the aralkanoyl or aroyl groups preferably containing not more than 20 1 carbon atoms and being optionally substituted by one or more C$_{1-6}$ alkoxy groups, halogen atoms, nitro groups, C$_{1-10}$ acyloxy or C$_{2-7}$ carboalkoxy groups), tri(hydrocarbyl) silyl, (in which the silyl group carries three hydrocarbon substituents, which may be the same or different, selected from C$_{1-6}$ alkyl, C$_{5-20}$ aralkyl and C$_{4-20}$ aryl groups), or tetrahydropyranyl.

Specific examples of the groups $R^1$ or $R^2$ include t-butyl, 2,2,2-trichloroethyl, methoxymethyl, t-butoxymethyl, 2,2,2-trichloroethoxymethyl, 2-methoxyethoxymethyl, 1-methoxyethyl, 1-ethoxyethyl, 2-(trimethylsilyl)ethoxymethyl, benzyloxymethyl,methoxycarbonyl, ethoxycarbonyl, isobutyloxycarbonyl, 2,2,2-trichloroethoxycarbonyl, benzyl, p-methoxybenzyl, o-nitrobenzyl, p-nitrobenzyl, p-chlorobenzyl, p-bromobenzyl, diphenylmethyl, triphenylmethyl, p-methoxyphenyldiphenylmethyl, formyl, acetyl, monochloroacetyl, dichloroacetyl, trichloroacetyl, trifluoroacetyl, trimethylacetyl, methoxyacetyl, phenoxyacetyl, p-chlorophenoxyacetyl, isobutyryl, benzoyl, p-nitrobenzoyl, triethylsilyl, isopropyldimethylsilyl, t-butyldimethylsilyl, t-butyldiphenylsilyl, methyldi-t-butylsilyl, (triphenylmethyl)dimethylsilyl, triphenylsilyl and tetrahydropyranyl.

A particularly useful protecting groupo represented by $R^1$ and $R^2$ is benzyl.

The protecting groups $R^1$ and $R^2$ may be removed, where appropriate, by the addition of either an acid or a base, or by reduction. Thus, for example, an alkyl, trihydrocarbylsilyl or tetrahydropyranyl group may be removed by acid hydrolysis, e.g. with a mineral acid or trifluoroacetic acid. Alkoxycarbonyl and acyl groups may be removed by alkaline hydrolysis. Arylmethyl groups may be removed by reduction, for example by hydrogenolysis, for example with hydrogen and a catalyst such as palladium on a support such as charcoal in a solvent such as a lower alkanol e.g. methanol or ethanol, an ester e.g. ethyl acetate or an ether e.g. tetrahydrofuran, or with a Lewis Acid such as aluminium trichloride in a solvent such as toluene.

The deprotection reaction may be performed in situ following the cyclisation of the compound of formula (IIa) or (IIb). Alternatively, if desired, after the cyclisation has been effected, the resulting protected diol of formula (III) may first be isolated, before subsequent reaction to yield the diol of formula (I).

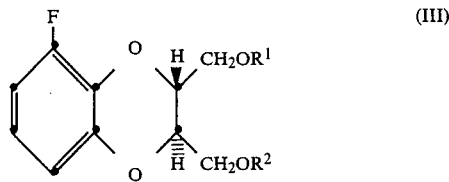
(III)

According to another feature of the present invention the diol of formula (I) (prepared from intermediate (IIa) or (IIb)) may be used to prepare (±) trans-5-fluoro-2,3,3a,9a-tetrahydro-1H-[1,4]-benzodioxino[2,3-c]pyrrole (VI) by the following reaction sequence:

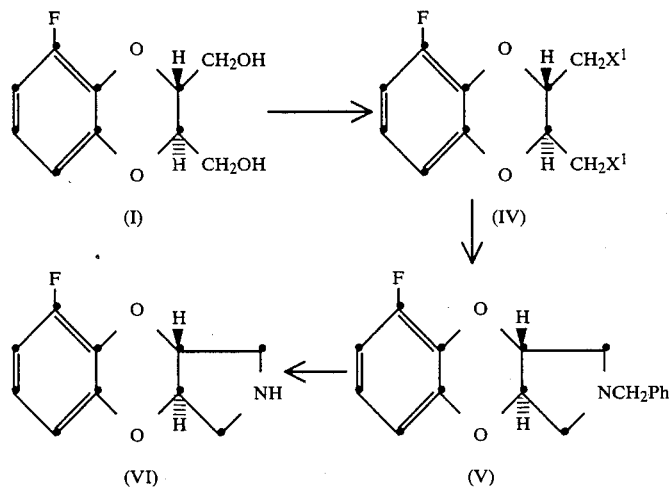

In formula (IV) above $X^1$ represents a leaving group such as alkanesulphonate or halogen. A compound of formula (IV) in which $X^1$ represents alkanesulphonate may be prepared by reacting a diol (I) with a hydrocarbylsulphonyl halide eg methanesulphonyl chloride in the presence of a base such as triethylamine. A compound of formula (IV) in which $X^1$ represents halogen may be prepared by reacting a diol (I) with a suitable halogenating agent. Amination of (IV) using benzylamine gives the compound of formula (V). Hydrogenolysis of the compound (V) using hydrogen and palladium on charcoal yields the desired compound of formula (VI). The compound (VI) may be converted to an acid addition salt e.g. the hydrochloride salt by addition of an appropriate acid e.g. hydrochloric acid in a suitable solvent.

The corresponding N-alkyl derivatives may be similarly prepared by reacting a compound of formula (IV) with a suitable alkylamine.

The compounds of formulae (IIa) or (IIb) may be prepared according to the following reaction sequence, which sequence also constitutes a further feature of the present invention.

Thus, the compounds of formulae (IIa) and (IIb) wherein X represents a halogen atom such as chlorine may be prepared from the appropriate dihydroxy compounds of formulae (VIIa) and (VIIb) or a mixture thereof.

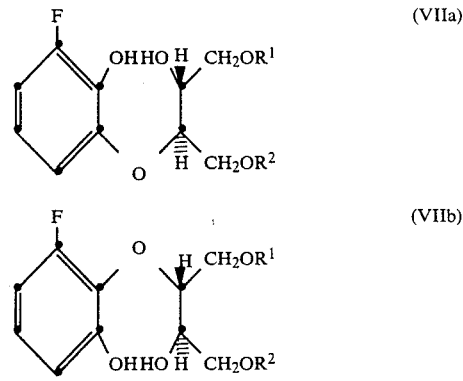

(wherein $R^1$ and $R^2$ are as previously defined)

The reaction may be effected using suitable halogenating conditions, for example using oxalyl chloride, thionyl chloride or phosgene in the presence of dimethylformamide. The reaction is preferably carried out in a solvent such as a halogenated hydrocarbon eg. methylene chloride or an aromatic hydrocarbon eg. toluene at a temperature in the range of from room temperature to reflux. The reaction may also be carried out in an ether such as dioxane.

The compounds of formulae (IIa) and (IIb) and (VIIa) and (VIIb) are novel compounds and constitute a further feature of the present invention.

The compounds of formulae (VIIa) and (VIIb) may also be converted to a compound of formula (I) via the in situ preparation of a compound of formula (IIa) or (IIb).

The compounds of formulae (IIa) and (IIb) wherein X represents a hydroxyl group may be prepared from the trans oxido compound (VIIIa) and the corresponding trans isomers of formulae (VIIa) and (VIIb) may be prepared from the cis oxido compound (VIIIb)

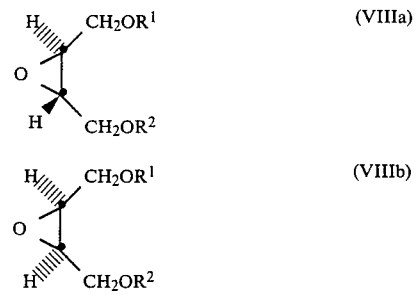

(wherein $R^1$ and $R^2$ are as previously defined) by reaction with 3-fluorobenzene-1,2-diol.

The reaction may be carried out in the presence of a suitable base such as an alkali metal hydride (eg sodium hydride), an alkali metal alkoxide (eg sodium ethoxide or potassium tert-butoxide) or, more particularly, an alkali metal carbonate (eg sodium carbonate or potassium carbonate) at elevated temperatures eg 130° C. and optionally in the presence of a solvent. Suitable solvents for the reaction include amides such as dimethylformamide and alcohols such as n-propanol optionally with water added as a cosolvent. A mixed solvent system such as dimethylformamide/toluene may also be used.

The oxido compounds of formulae (VIIIa) and (VIIIb) and either known compounds or may be prepared by the methods described by R. C. Forster and L. N. Owen J. Chemical Soc. Perkin Trans. 1, 1978, 8, 822–829.

The following examples illustrate the invention. All temperatures are in ° C. In general, reactions were monitored by thin layer chromatography (t.l.c.), reaction mixtures and isolated products being compared with authentic samples of starting materials and products.

Intermediate 1

(R*,R*)-(±)-3-Fluoro-
2-[2-hydroxy-3-(phenylmethoxy)
-1-[(phenylmethoxy)methyl]propoxy]phenol and
(R*,R*)-(±)-6-fluoro-2-[2-hydroxy-3-(phenylmehoxy)-
1-[(phenylmethoxy)methyl]-propoxy]phenol
3-Fluorobenzene-1,2-diol (57 g) and (cis)-bis

[(phenylmethoxy)methyl]oxiran (57 g) were heated under reflux with sodium carbonate (22 g) in propan-1-ol (150 ml) and water (150 ml) for 18 h. The cooled dark brown mixture was partitioned between toluene (300 ml) and water (300 ml) and the layers were separated. The aqueous layer was e-extracted with toluene (300 ml) and the toluene solutions were sequentially washed with 5% aqueous sodium carbonate (100 ml) adjusted to pH 9 with acetic acid (5 ml), and with saturated sodium bicarbonate solution (100 ml). The toluene solutions were combined and treated with charcoal (5.7 g) for 2 h. The charcoal was filtered off and washed with toluene (2×50 ml). The combined filtrates were evaporated in vacuo to give an orange-brown oily mixture of the title compounds (74.5 g)..

Intermediate 2

(R*,R*)-(±)-3-fluoro-2-[2-hydroxy-3-(phenylmethoxy)-1-[(phenylmethoxy)methyl]propoxy]phenol
(Compound A) and
(R*,R*)-(±)-6-fluoro-2-[2-hydroxy-3-(phenylmethoxy)-1-[(phenylmethoxy)methyl]propoxy]phenol
(Compound B)

Repetition of the procedure described in Intermediate 1 gave a mixture of the title compounds (82 g). This was chromatographed over Sorbsil (750 g) in light petroleum (b.p 40/60)-ethyl acetate (3:1). Elution of the column with the same solvent mixtures (7°) followed by light petroleum (b.p 40°–60°)-ethyl acetate (2:1) (8l) and combination of appropriate fractions gave the 3-fluoro isomer (20.2 g) and the 6-fluoro isomer (9.9 g).

The 3-fluoroisomer had $V_{max}$ (in $CHBr_3$) 3700–2600 (OH) 1620, 1590, 1492cm$^{-1}$ (aromatic) δ (in $CDCl_3$), 7.4–7.2 (10H, m) (benzyl $C_6H_5$), 6.95 (1H, m) (5-H), 6.75 (1H, m) (6-H), 6.60 (1H, m) (4-H), 5.0–4.4 (4H, m) (benzyl $CH_2$) 4.3–4.0 (2H, m) (aliphatic $CH_2$).

The 6-fluoroisomer had $V_{max}$ (in $CHBr_3$) 3650–2600 (OH), 1620, 1595, 1493cm$^{-1}$ (aromatic); δ (in $CDCl_3$) 7.30 (10H, m) (benzyl $C_6H_5$), 6.9–6.6 (3H, m) (3,4,5-H's), 4.7–4.3 (4H, m) (benzyl $CH_2$), 4.20 (2H, m) (aliphatic CH's), and 3.8–3.4 (4H, M) (aliphatic $CH_2$'s)

Intermediate 3

(R*,S*)-(±)-2-[2-Chloro-3-(phenylmethoxy)-1-[(phenylmethoxy)methyl]propoxy]-3-fluorophenol and
(R*,S*)-(±)-2-[2-chloro-3-(phenylmethoxy)-1-[(phenylmethoxy)methyl]propoxy]-6-fluorophenol Oxalyl chloride (20 ml) was slowly added to a stirred solution of dimethylformamide (20 ml) in toluene (400 ml). The resultant slurry was stirred for 10 minutes and a solution of the mixed isomers from Intermediate 1 (74.6 g) in toluene (375 ml) was added over 10 minutes. The mixture was heated to reflux for 60 minutes. After being cooled to 25°, the resultant dark brown solution was washed with a mixture of 3% aqueous sodium bicarbonate solution (450 ml) and 30% aqueous sodium chloride solution (100 ml) followed by 10% aqueous sodium chloride solution (300 ml). The washes were re-extracted with toluene (200 ml) and the toluene solutions were combined and evaporated to give a mixture of the title componds as a brown oil (77.7 g).

Intermediate 4

(R*,S*)-(±)-2-[2-Chloro-3-(phenylmethoxy)-1-[(phenylmethoxy)methyl]propoxy]-3-fluorophenol Oxalyl chloride (5.5 ml) was added dropwise to a stirred solution of dimethlformamide (5.5 ml) in dry toluene (200 ml) at ambient temperature. The resultant suspension was stirred for 5 minutes, then a solution of Compound A in Intermediate 2 (17.8 g) in toluene (150 ml) was slowly added to it. The resultant yellow solution was then refluxed for 1.3 h and cooled. The mixture was washed with water (3×100 ml), saturated sodium bicarbonate (50 ml) and evaporated to give the title compound as a brown oil (18.5 g) which had $V_{max}$(in CHBr$_3$) 3280 (OH), 1618, 1591, 1492cm$^{-1}$ (aromatic); δ (in CDCl$_3$) 8.00 ( 11 H, s) (OH), 7.5–7.3 (10H, m) Benzyl C$_6$H$_5$), 6.98 ( 11 H, m) 5-8), 6.77 ( 11 H, m) (6-H), 6.63 (1H, m) (4-H), 4.8–4.5 (5H, m) (benzyl CH$_2$'s +>CH-O, 4.38 (1H, m) (>CH-Cl), and 4.1–3.6 (aliphatic CH$_2$'s).

The oily product obtained from another similar experiment was crystallized from di-isopropyl ether to give the title compound as prisms, m.p. 77°–79°.

Intermediate 5

Preparation of (R*,S*)-(±)-2-[2-Chloro-3-(phenylmethoxy)-1-[(phenylmehoxy)methyl]propoxy]-6-fluorophenol Oxalyl chloride (1.7 ml) was added dropwise to a stirred solution of dimethylformamide (1.7 ml) in toluene (60 ml) at ambient temperature. After the resultant suspension had been stirred for 10 minutes, a solution of Compound B in Intermediate 2 (7.6 g) in toluene (70 ml) was slowly added. The mixture was refluxed for 50 minutes, cooled, washed with water (2×50 ml) and saturated sodium bicarbonate (25 ml), and evaporated in vacuo to give a yellow oil. The oil was dissolved in dichloromethane (20 ml) and percolated through a column of Sorbsil (10 g) and the column was eluted with more dichloromethane (25 ml). Evaporation of the combined eluates gave the title compound as a yellow oil (70.0 g) which had $V_{max}$(in CHBr$_3$) 3600–2600 (OH), 1621, 1595, 1495cm$^{-1}$ (aromatic); δ (in CDCl$_3$) 7.46 ( 11 H, s) (OH), 7.4–72 (10H, m) (benzyl C$_6$H$_5$), 7.0–6.6 (3H, m) (3,4,5-H's) 4.65 (4H, m) (benzyl CH$_2$'s), 4.45 (aliphatic CH's) and 4.1–3.6 (aliphatic CH$_2$'s).

Intermediate 6

(R*S*)-(±)-3-Fluoro-[2-2-hydroxy-3-(phenylmethoxy)-1-[(phenylmethoxy)methyl]propoxy]phenol (Compound C) and (R*,S*)-(±)-6-fluoro-2-[2-hydroxy-3-(phenylmethoxy)-1-[(phenylmethoxy)-methyl]propoxy]phenol (Compound D)

A mixture of 3-fluorobenzene-1,2-diol (6 g), (trans)-bis[(phenylmethoxy)methyl oxiran (5.72 g), anhydrous potassium carbonate (1.4 g) and dimethylformamide (10 ml) was stirred at 142° for 2 h. When cool, the mixture was partitioned between toluene (100 ml) and 1M hydrochloric acid (50 ml) and allowed to separate. The aqueous layer was backwashed with toluene (50 ml). The organic layers were washed sequentially with M hydrochloric acid (50 ml) and saturated sodium bicarbonate solution (2×50 ml). The combined organic layers were evaporated to give a dark oil containing the title compounds. The oil was dissolved in dichloromethane (10 ml) and chromatographed on Sorbsil (200 g) in dichloromethane. Elution was 4% ethyl acetate in dichloromethane separated the title compounds. Evaporation of the appropriate early and later fractions gave respectively the 3-fluoroisomer (4.0 g) and the 6-fluoroisomer (1.16 g) as oils.

The 3-fluoroisomer had δ (in CDCl$_3$), 8.18 ( 11 H, s) (phenolic OH), 7.30 (10H, s) (benzyl C$_6$H$_5$), 7.1–6.4 (3H, m) (4,5,6-H's), 4.6–4.4 (4H, d) Ibenzyl CH$_2$), 3.04 (1H, 7Hz) (aliphatic OH), 4.4–3.5 (6H, m) (aliphatic CH's and CH$_2$'s).

The 6-fluoroisomer had δ (in CDCl$_3$), 7.73 (1H, s) (phenolic OH), 7.28 (10H, s) (benzyl C$_6$H$_5$), 7.0-6.4 (3H, m) (3,4,5-H's), 4.6–4.5 (4H, d, benzyl CH$_2$), 4.10 (1H, broad s) (phenolic OH), 4.0–3.5 (6H, m) (aliphatic CH's and CH$_2$'s).

Intermediate 7

(±)-trans-5-Fluoro-2,3-dihydro-2,3-bis[(phenylmethoxy)-methyl]-1,4-benzodioxin (a) A solution of mixed chlorophenol compounds prepared in Intermediate 3 (77.7 g) in acetone (780 ml) was refluxed and stirred under nitrogen with potassium carbonate (77.8 g) for 3 h. The mixture was cooled and the solid was filtered off and washed with acetone (3×75 ml). The combined filtrates were evaporated to give a brown oil. This was dissolved in dichloromethane (200 ml) and chomatographed over Sorbsil (140 g). Elution with more dichloromethane (800 ml) and evaporation of the combined eluates gave the title compound as a pale yellow oil (58.4 g).

(b) A solution of Intermediate 4 (18.1 g) in acetone (180 ml) was stirred and refluxed with potassium carbonate (18.1 g) for 3.5 h. The mixture was cooled, the solids were filtered off and the filter was washed with acetone (3×3.25 ml). The combinend filtrates were evaporated in vacuo to a yellow oil which was dissolved in dichloromethane (50 ml) and percolated through a column of Sorbsil (30 g). Elution of the column with more dichloromethane (300 ml) and evaporation of the combined eluates afforded the title compound as an almost colourless oil (13.9 g).

(c) Dichloromethane (15 ml) and dimethylformamide (0.64 ml) were stirred and cooled to 3°. Oxalyl chloride (0.64 ml) in dichloromethane (5 ml) was added cautiously. After stirring for 10 minutes the Compound C in Intermediate 6 (3 g) was dissolved in dichloromethane (5 ml) and added over 10 minutes keeping the temperature below 5°. After a further 10 minutes triethylamine (5.5 ml) was added, below 5°. The mixture was stirred at 45° for 18 h and after cooling, water (20 ml) was added. The layers were separated and the aqueous layer was washed with dichloromethane (20 ml). The organic layers were washed sequentially with M hydrochloric acid (2×25 ml) and 30% sodium chloride solution (25 ml). Evaporation of the combined organic layers gave a dark brown oil. This was chromatographed on Sorbsil (60 g) in 9:1 60/80 petrol/dichloromethane to give the title compound (2.2 g).

(d) A solution of Inermediate 5 (6.8 g) in acetone (80 ml) was stirred and refluxed with potassium carbonate (6.8 g) for 4 h. The mixture was cooled, the solids were filtered off and the filter was washed with acetone (2×20 ml). The combined filtrates were evaporated to an oil which was dissolved in dichloromethane (20 ml) and percolated through a column of Sorbsil (14 g). Elution of the column with more dichloromethane (150 ml) and evaporation of the combined eluates afforded the title compound as an oil (5.7 g).

(e) According to the process described in part (d) above, Compound D in Intermediate 6 (2.2 g) gave the title compound (2.2 g).

(f) An extract of the mixed chlorophenol compounds prepared in Intermediate 3 (34.5 g) in toluene (230 ml) was stirred for 4 hr at 80° with a solution of potassium carbonate (12 g) in water (25 ml) containing tetrabutylammonium iodide (1 g). The mixture was allowed to cool to ambient temperature and stirring was continued overnight by which the time tlc [using 3:2 dichloromethane-petroleum petroleum ether (b.p. 60°-80°) as eluant]revealed that formation of the title compound (Rf. 0.3) was essentially complete.

Intermediate 8

(±)-trans- 5l -fluoro- 2,3-dihydro-2,3-bis[(phenylmethoxy) methyl]-1,4-dioxin

A mixture of the chlorophenol compounds prepared in Intermediate 3 (10.3 g), water (19.1 ml), potassium carbonate (7.9 g) and tetrabutylammonium iodide (0.41 g) was stirred and heated for 1.5hr on a steam bath. The mixture was cooled, extracted with di-isopropyl ether (24 ml) and the separated organic extract was washed successively with 2M sodium hydroxide solution (2×12 ml) and M hydrochloric acid (12 ml). Evaporation of the organic extract afforded as amber oil (8.6 g). This was dissolved in methanol (17 ml), seeded and stirred at ambient temperature for 0.5hr. After refrigerating at 0° overnight the product was filtered off, washed with cold methanol and dried in vacuo to give the title compound (5.26 g), m.p. 61.5°-63°. $\delta$(CDCl$_3$, 7.4–7.2 (10H, m, Ph), 6.8–6.6 (3H, m, 6-H, 7-H, 8-H), 4.58 and 4.46 (4H, AB$_q$, CH$_2$-Ph), 4.34 (2H, m, 2-H, 3-H), 3.9–3.6 (4H, m, CH$_2$O).

Intermediate 9

(±)-trans-5-fluoro-2,3-dihydro-2,3-bis[(phenylmethoxy)methyl]-1,4-dioxin

A mixture of chlorophenols prepared in Intermediate 3 (35.2 g) was vigorously stirred with tricaprylylmethyl ammonium chloride (Aliquat 336, chloride form) (1.6 g) and potassium carbonate (29 g) in water (70 ml) at ca. 95° under nitrogen for 80 minutes. The dark brown mixture was cooled and extracted with di-isopropyl ether (2×100 ml). The organic solutions were sequentially washed with 2.5M aqueous sodium hydroxide solution (2×50 ml), M aqueous hydrochloric acid (100 ml), combined and evaporated to a brown oil (33.5 g). This was stirred vigorously for 1 hour with methanol (65 ml) at 22° and the resultant slurry was chilled (ca. 4°) overnight. The crystals were harvested, washed with chilled methanol and dried in vacuo to afford the title compound as off-white prisms (20.2 g), m.p. 61.5°-63°.

EXAMPLE 1

(±)-trans-5-Fluoro-2,3-dihydro-1,4-benzodioxin-2,3-dimethanol

A solution of the compound of Intermediate 7 (58.4 g) in IMS (600 ml) was stirred at ca. 50° under hydrogen with 4.7% palladium-on-charcoal paste (23 g) until uptake became very slow. The catalyst was filtered off and washed with IMS (2×50 ml). The combined filtrates were evaporated in vacuo to a syrup which was diluted with toluene (350 ml) and stirred. The resulting suspension was partially evaporated in vacuo and cooled to 25°. The crystals were harvested, washed with toluene (2×50 ml), 5:1 toluene-ethyl acetate (120 ml) then 3:1 toluene-ethyl acetate, and finally with toluene (100 ml) and dried at 40° in vacuo to afford the title compound as white needles (20.4 g) m.p 123°-124°.

EXAMPLE 2

(±)-(trans)-5-Fluoro-2,3-dihydro-1,4-benzodioxin-2,3-dimethanol, bismethanesulphonate A solution of the compound of Example 1 (3.10 g) in dichloromethane (30 ml) and triethylamine (6.4 ml) was stirred for 10 min, with ice-bath cooling. A solution of methanesulphonyl chloride (3.2 ml) in dichloromethane (10 ml) was added during 10 min. and the resultant suspension was stirred for 30 min. Water (25 ml) was added and the mixture was stirred for 20 min, the layers were then separated and the aqueous layer was re-extracted with dichloromethane (25 ml). The organic solutions were washed with water (25 ml, and were combined and evaporated to an oil which was chromatographed over Sorbsil (40 g), eluting with 9:1 dichloromethane-ethyl acetate. Appropriate fractions were combined and evaporated to a pale yellow oil (5.9 g) which crystallised from ethyl acetate—di-isopropyl ether to afford the title compound as prisms (4.15 g) m.p. 65.5°-67.5°. NMR $\tau$(CDCl$_3$) 3.1–3.35 (3H, m, aromatic), 5.3–5.5 (4H, m, CH$_2$O) 5.5–5.65 (2H, m, 2-H,3-H) 6.89, 6.91 (6H, singlets, CH$_3$SO$_3$).

EXAMPLE 3

(±)-(trans)-5-Fluoro-2,3,3a,9a-tetrahydro-2-(phenylmethyl)- 1H-[1,4]benzodioxino[2,3-c]pyrrole A homogenised mixture of phenylmethanamine (8 ml) and the compound of Example 2 (5.3 g) was heated to 130° for 15 min. then cooled to 25°, and partitioned between di-isopropyl ether (80 ml) and water (80 ml). The aqueous layer was re-extracted and di-isopropyl ether (100 ml) and the organic solutions were sequentially washed with 12.5% aqueous acetic acid (2×50 ml) and 15% aqueous sodium chloride (100 ml) containing sodium hydrogen carbonate (5 g). They were then combined and evaporated in vacuo to an orange-brown oil (3.8 g) which crystallised spontaneously. This was recrystallised from di-isopropyl ether - light petroleum (1:1) to give pink crystals of the title compound (2.9 g) Chromatography of the mother liquor gave a further crop (0.6 g). A recrystallised sample, m.p. 80°-81° had the following analysis: Found: C,71.7; H,5.65; N,4.95; F,6.8 C$_{17}$H$_{16}$FNO$_2$ requires: C,71.6; H,5.65; N,4.9; F,6.65%

EXAMPLE 4

(±)-(trans)-5-Fluoro-2,3,3a,9a-tetrahydro-1H-[1,4]benzodioxino[2,3-c]pyrrole hydrochloride A solution of the compound of Example 3 (2.3 g) in industrial methylated spirits (IMS) (110 ml) was stirred under hydrogen at ca. 25° with 5% palladium on charcoal (1.15 g) until uptake ceased (270 ml). The catalyst was filtered off using a kieselguhr pad, the filter was washed through with IMS (3×20 ml) and the combined filtrates were evaporated in vacuo to a pale pink oil (1.6 g). This was re-dissolved in IMS (10 ml) and 10M hydrochloric acid (1 ml) was added. After 30 min. at 20°, the resultant white crystals were harvested, washed with IMS (3 ml), 1:1 IMS -di-isopropyl ether (4 ml) and di-isopropyl ethe (2×5 ml) to afford the title compound as a hemi-hydrate, (1.09 g) m.p. ca. 245° (sublimes above 210°) NMR $\tau$(DMSO-d$_6$) −0.25 (2H, broad s, NH$_2$+), 2.9–3.2 (3H, m, 6-H, 7-H and 8-H), 5.4–5.6 (2H, m, 3a-H, 9a-H), 6.0-6.3, 6.6-6.8 (4H, ABq, 1-H$_2$, 3-H$_2$).

We claim:

1. A process for the preparation of (±) trans-5-fluoro- 2,3,3a,9a-tetrahydro- 11 H-(1,4)-benzodioxino-( 2,3-c)pyrrole by a multi-stage process comprising (a) cyclising a compound of formula (IIa) or (IIb):

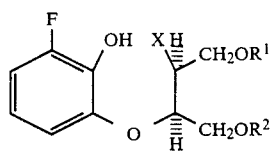

(IIa)

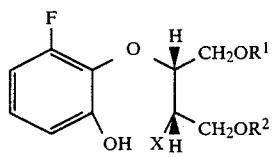

(IIb)

or a mixture thereof (in which X represents a hydroxyl group or a halogen atom and $R^1$ and $R^2$, which may the same or different, represent hydroxy protecting groups), wherein (i) when x represents a hydroxyl group the cyclisation is effected using a disubstituted formamide in the presence of a reagent selected from oxalyl chloride, thionyl chloride, phosgene and phosphorous oxychloride in the presence of a base, or a triarylphosphine, a trialkylphosphine or a trialylphosphite in the presence of diethylazodicarboxylate, or a triarylphosphine or trialkylphosphine in the presence of carbon tetrachloride, or (ii) when X is a halogen atom the cyclisation is effected in the presence of a base, and (b) removal of the protection groups $R^1$ and $R^2$;

(c) reacting the resulting compound of formula (I):

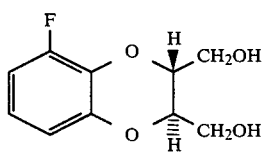

(I)

with a reagent capable of replacing the hydroxyl groups with leaving groups;

(d) aminating the resulting compound of general formula (IV):

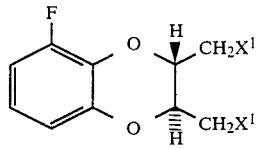

(IV)

(where $X^1$ represents a leaving group) with benzylamine;

(e) subjecting the resulting compound of formula (V):

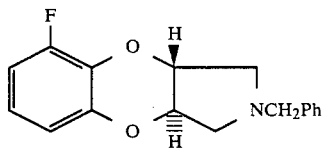

(V)

to hydrogenolysis to produce the desired compound (VI):

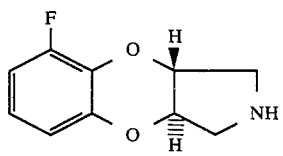

(VI)

and, if desired, reacting the resulting compound of formula (VI) with an acid to produce the acid addition salt thereof.

2. A process according to claim 1 in which a compound of general formula (IIa) or (IIb) or a mixture thereof is prepared by halogenating an appropraite dihydroxy compound of formula (VIIa) or (VIIb):

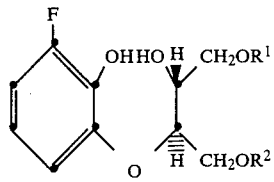

(VIIa)

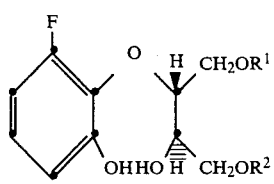

(VIIb)

in which $R^1$ and $R^2$ are the same or different and represent hydroxy protecting groups.

* * * * *

UNITED STATES PATENT AND TRADEMARK OFFICE
CERTIFICATE OF CORRECTION

PATENT NO. : 4,837,336

DATED : June 6, 1989

INVENTOR(S) : Hayman et al.

It is certified that error appears in the above-identified patent and that said Letters Patent is hereby corrected as shown below:

Claim 1, Column 11, line 2, change "11 H" to -- 1 H --.

Signed and Sealed this

Twenty-ninth Day of May, 1990

Attest:

HARRY F. MANBECK, JR.

Attesting Officer     Commissioner of Patents and Trademarks

UNITED STATES PATENT AND TRADEMARK OFFICE
CERTIFICATE OF CORRECTION

PATENT NO. : 4,837,336

DATED : June 6, 1989

INVENTOR(S) : Hayman, et al.

It is certified that error appears in the above-identified patent and that said Letters Patent is hereby corrected as shown below:

Claim 1, Column 11, lines 2-3 change

"(1,4)-benzodioxino-(2,3-c)pyrrole"

to -- [1,4]benzodioxino[2,3-c]pyrrole --.

Claim 1, Column 11, line 11, change

"which may the same or different" to

-- which may be the same or different --.

Signed and Sealed this

Tenth Day of July, 1990

Attest:

HARRY F. MANBECK, JR.

Attesting Officer     Commissioner of Patents and Trademarks